United States Patent [19]

Ioannides et al.

[11] Patent Number: 5,294,023
[45] Date of Patent: Mar. 15, 1994

[54] SYSTEM FOR DELIVERING LIQUID AT A CONTROLLED FLOW RATE

[75] Inventors: Antonis C. Ioannides; Alan Pindar, both of Abingdon Oxon, United Kingdom

[73] Assignee: Oxford GlycoSystems Limited, Oxon, United Kingdom

[21] Appl. No.: 765,386

[22] Filed: Sep. 25, 1991

[30] Foreign Application Priority Data

Sep. 27, 1990 [GB] United Kingdom ............... 9021094

[51] Int. Cl.5 ........................................... B67D 5/08
[52] U.S. Cl. ........................................... 222/61; 222/64
[58] Field of Search ............... 222/52, 59, 61, 64, 222/65, 66, 641

[56] References Cited

U.S. PATENT DOCUMENTS

| | | | |
|---|---|---|---|
| 3,459,333 | 8/1989 | Inglefield | 222/64 |
| 3,876,107 | 4/1975 | Meindl et al. | 222/64 |
| 4,274,552 | 6/1981 | Proni | 222/61 |
| 4,284,210 | 8/1981 | Horak | 222/14 |
| 4,580,699 | 4/1986 | Black et al. | 222/64 |
| 5,012,955 | 5/1991 | Shannon | 222/61 |

Primary Examiner—Kevin P. Shaver
Attorney, Agent, or Firm—Spencer, Frank & Schneider

[57] ABSTRACT

A liquid delivery system which can deliver liquid from a pressurized vessel holding a volume of the liquid, out through an outlet under a controlled pressure, thereby controlling the delivery rate of the liquid. The vessel can be re-filled while controlled liquid delivery continues, either by re-filling directly into the vessel and allowing any excess of pressure to be relieved, or by using a second pressurized vessel and continuing delivery from one vessel while the other is re-filled.

13 Claims, 4 Drawing Sheets

SYSTEM FOR DELIVERING LIQUID AT A CONTROLLED FLOW RATE

BACKGROUND OF THE INVENTION

This invention relates to a system for use in an application such as liquid chromatography, for delivering liquid at a controllable, constant flow rate.

SUMMARY OF THE INVENTION

According to the invention there is provided a system for delivering liquid at a controlled flow rate, the system comprising a vessel having an internal volume capable of being pressurized by a gas, said volume being adapted to receive a liquid, an outlet from said vessel arranged for delivery of said liquid under said pressure from said vessel, means for measuring the rate of flow of liquid out of the vessel and a controller for controlling the gas pressure in accordance with a signal from said measuring means so as to control the rate of liquid flow.

BRIEF DESCRIPTION OF THE DRAWINGS

Embodiments of the invention will now be described, with reference to the accompanying drawings, in which.

DESCRIPTION OF THE PREFERRED EMBODIMENTS

Figure 1:
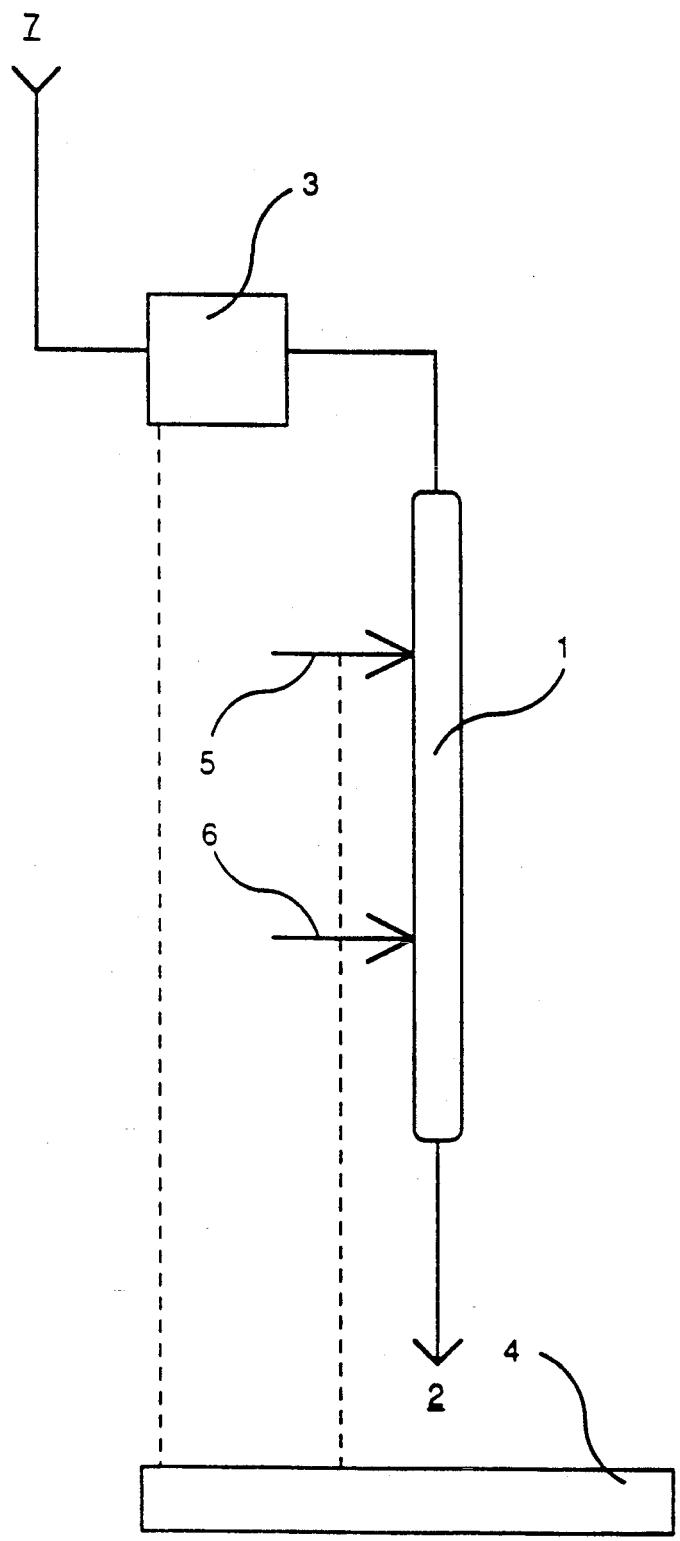
FIG. 1 is a diagram of a basic solvent delivery system constructed in accordance with the invention, and, FIG. 2 is a diagram of the solvent delivery system of FIG. 1 with a facility for re-filling.

FIG. 1 shows a system for delivering liquid, such as a liquid solvent, from a vessel 1 through an outlet 2 at a controllable rate. Vessel 1 is pressurized by gas delivered at a controlled pressure from a pressure regulating system 3, so that liquid is forced out through outlet 2 under this controlled pressure and will flow at a substantially controlled rate, subject only to variations in the resistance to flow of the load (not shown) to which liquid is being delivered.

The pressure applied to vessel 1 from pressure regulating system 3 is controlled by a control system 4 which monitors the flow of liquid and thereby controls gas delivery, from pressure regulating system 3. System 4 keeps the gas at the required pressure as the liquid level in vessel 1 falls with delivery of liquid through outlet 2, and will continue to control the pressure to the required level even if the resistance to flow of the load changes. Also, the rate of liquid delivery can be altered as desired, by altering the gas pressure, under the control of system 4.

As liquid is delivered through outlet 2, the level of liquid in vessel 1 will fall from an upper acceptable level until it reaches a lower acceptable level. As liquid falls from the upper level the movement of the liquid is detected by an upper liquid level detector 5 and, as it reaches the lower level, by a lower liquid level detector 6. The time taken for the liquid level to fall from the upper detected level to the lower detected level gives a measure of the rate of liquid delivery to the load because the volume of liquid in vessel 1 between the two detectors 5, 6 is known. From this information the pressure delivered by system 3 may be adjusted more accurately to provide the required flow rate at outlet 2.

The pressure regulating system 3 receives a supply of pressurised gas from a high pressure source 7.

FIG. 1 shows the minimum system required for operation using liquid detectors as the means for measuring the rate of flow of the liquid.

Figure 2:
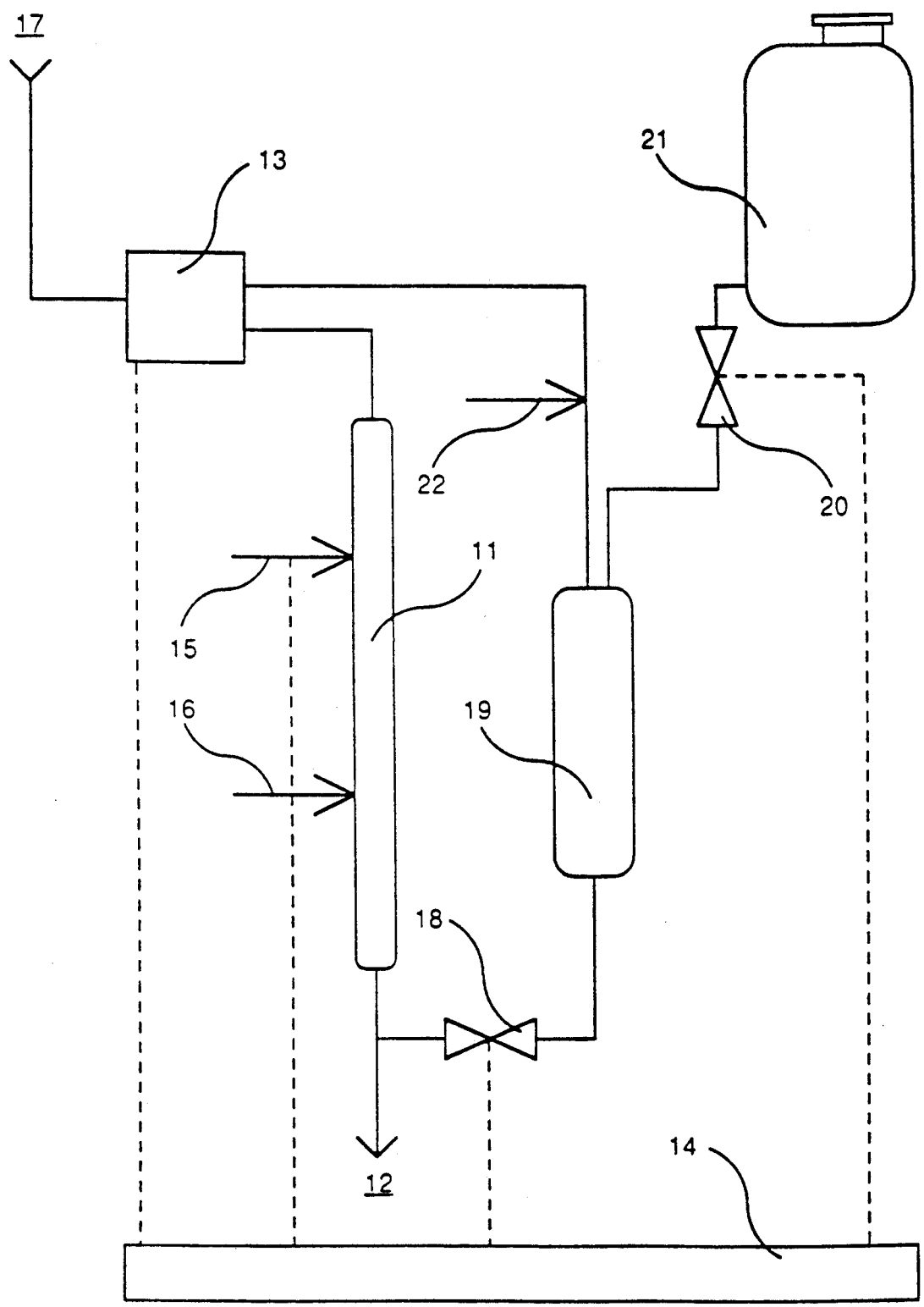

FIG. 2 shows a full system including an arrangement for re-filling the vessel with liquid. In FIG. 2 a vessel 11 is pressurized by gas delivered at a controlled pressure from a pressure regulating system 13 so that liquid is forced out through an outlet 12 under this controlled pressure and will flow at a controlled rate, subject only to variations in the resistance to flow of the load (not shown) to which liquid is being delivered. The pressure applied to vessel 11 from pressure regulating system 13 is controlled by a control system 14 which monitors the flow of liquid and thereby controls gas delivery from pressure regulating system 13. System 14 keeps the gas at the required pressure as the liquid level in vessel 11 falls with delivery of liquid through outlet 12, and will continue to control the pressure to the required level even if the resistance to flow of the load changes. Also, the rate of liquid delivery can be altered as desired, by altering the gas pressure, under the control of system 14. As liquid is delivered through outlet 12, the level of liquid in vessel 11 falls from an upper acceptable level until it reaches a lower acceptable level. As liquid falls from the upper level the movement of the liquid is detected by an upper liquid level detector 15 and as it reaches the lower level by a lower liquid level detector 16. The time taken for the liquid level to fall from the upper detected level to the lower detected level gives a measure of the rate of liquid delivery to the load because the volume of liquid in vessel 11 between the two detectors 15, 16 is known.

In the arrangement of FIG. 2, when the liquid reaches the lower liquid level detector 16, actuation of detector 16 causes the vessel 11 to be re-filled. During re-filling, liquid continues to be delivered through outlet 12 as the control system 14 causes pressure regulating system 13 to continue to apply the same previously controlled pressure to outlet 12.

To re-fill vessel 11, a valve 18 is opened allowing liquid to flow from a reservoir 19. Reservoir 19 is also pressurized from pressure regulating system 13 but at a slightly higher pressure than that applied to vessel 11. Thus, liquid flows from the reservoir 19 into vessel 11 to re-fill it whilst liquid also continues to be delivered through outlet 12 to the load. As filling continues the level of liquid in vessel 11 will rise until it reaches the higher acceptable level detected by liquid level detector 15. This detector is then actuated which causes valve 18 to be closed completing re-filling. Throughout the whole of the re-filling operation the liquid flow out through outlet 12 continues thus giving, at all times, an uninterrupted, pulsation-free, liquid delivery.

The control system 14 ensures that during re-filling the pressure in vessel 11 is not allowed to change from the required level and any change in pressure is immediately corrected by the pressure regulating system 13, so that liquid still flows out of outlet 12 at substantially the same rate. Volumetric flow can therefore be calculated because the amount of liquid delivered can be directly related to elapsed time. Alternatively, the volume of liquid delivered may be calculated from the volume of gas delivered by the pressure regulating system 13.

During re-filling, in order to cause the liquid to rise upwards in vessel 11 the pressure at the top of vessel 11 needs to be lower than the pressure at the bottom, i.e. at the outlet 12. As the pressure at outlet 12 must remain constant this is achieved by the pressure at the top of the vessel being lowered by the regulating system 13.

Figure 3:
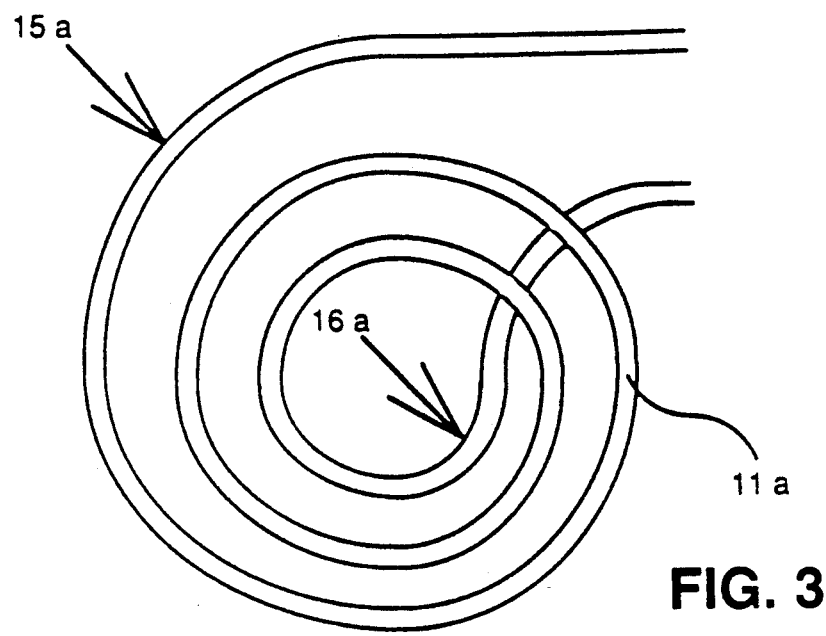
FIGS. 3 and 4 are respectively diagrammatic plan and elevation of an alternative detail of the system of FIG. 2.
Figure 4:
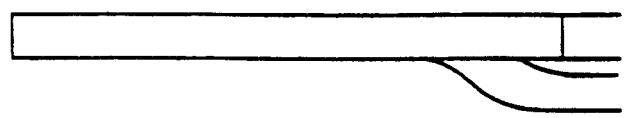

However, in order to reduce the vertical distance between the top and bottom of vessel 11, an alternative arrangement for the vessel 11 can be used. FIGS. 3 and 4 show such an arrangement in which the vessel 11a is placed horizontally and is coiled so as to occupy only a small space. The positions of upper detector 15a and lower detector 16a are shown. With this arrangement it is required that the inside diameter of the coiled tube shall be sufficiently small in relation to the surface tension of the liquid, that the liquid will not separate from the wall of the tube. In practice, with purified water, a diameter of no more than about 3 mm is needed but this diameter will be different with liquids of different surface tensions and/or densities.

Figure 5:
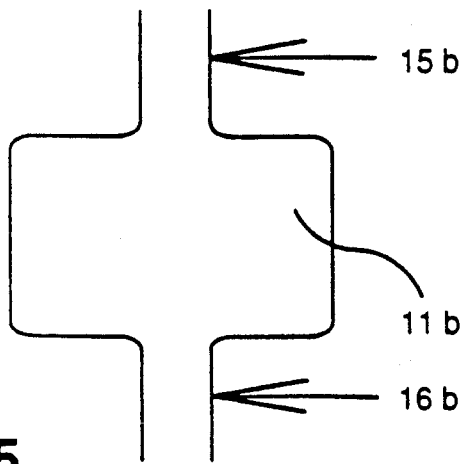
FIG. 5 is an elevation of a further alternative detail of the system of FIG. 2, and, FIG. 6 is a diagram of another system similar to that of FIG. 2.

FIG. 5 illustrates another alternative in which the center of the vessel 11b has been made bulbous thereby reducing the height of the vessel for a given volume, whilst maintaining the accuracy of upper and lower level detection. Upper detector 15b and lower detector 16b are shown.

During the re-filling of vessel 11, small perturbations of the pressure will occur at outlet 12 while the liquid level is restored to the upper level; these will be minimised by the alternatives shown in FIGS. 3, 4 and 5.

Reservoir 19 itself needs to be re-filled from time to time. This has to be done at a time when vessel 11 is not being re-filled. With valve 18 closed, a further valve 20 is opened to allow liquid to flow under gravity from a tank 21 whilst reservoir 19 is vented to atmosphere, through regulating system 13, until the level in reservoir 19 rises up the vent and the liquid level is detected by detector 22. Further valve 20 is then closed and reservoir 19 is repressurised from pressure regulating system 13. Whilst reservoir 19 is being re-filled detector 22 prevents overfilling but it also detects when the tank 21 runs short of liquid as the level in reservoir 19 will not reach detector 22. The system 14 controls the opening and closing of valves 18 and 20 and the flow of gas through the pressure regulating system which receives pressurized gas from a high pressure source 17.

Figure 6:
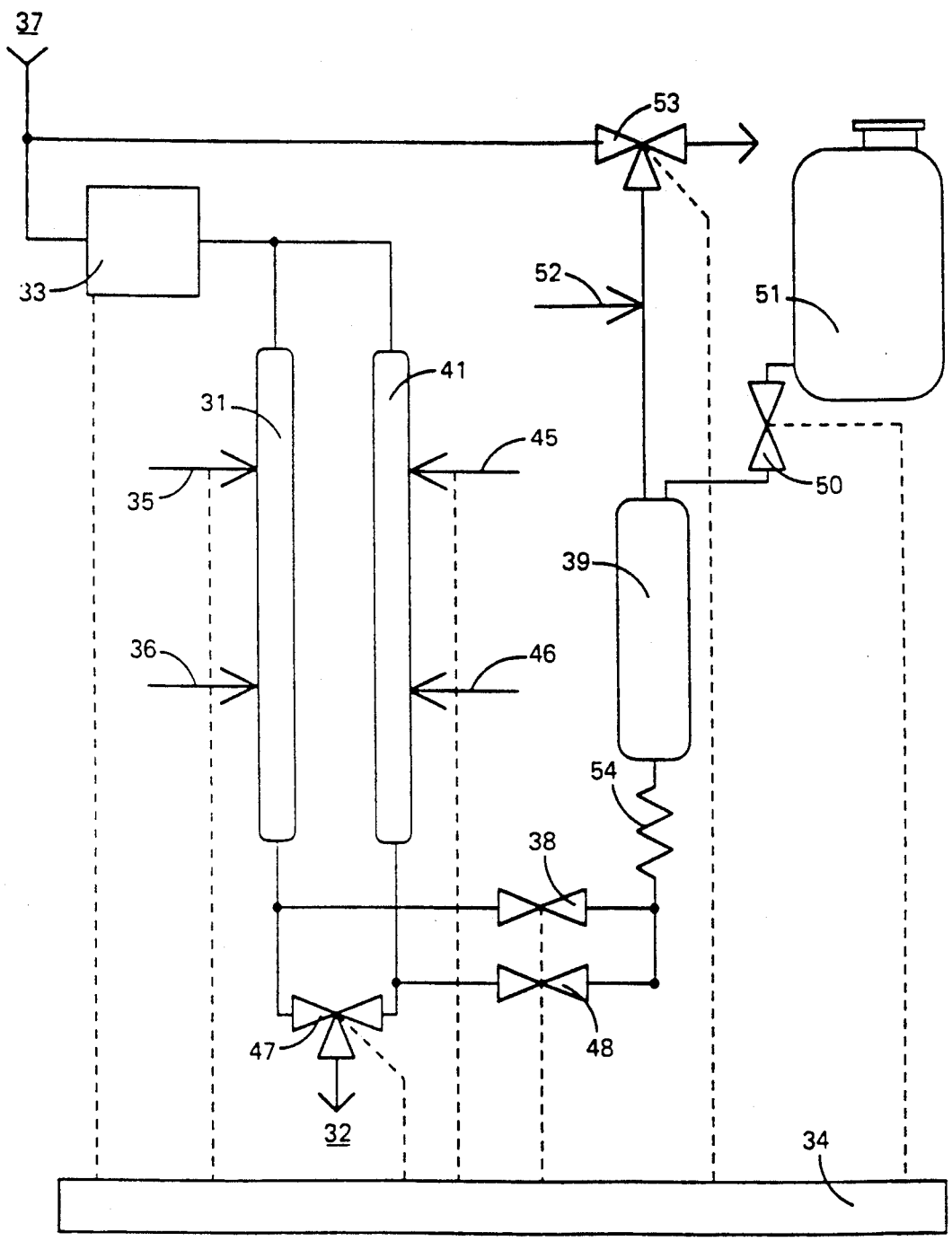

Referring now to FIG. 6, a system similar to that of FIG. 2 is shown for delivering liquid, such as a liquid solvent, either from a vessel 31 or a further vessel 41 through a common outlet 32. Considering vessel 31 first, this is pressurized by gas delivered at a controlled pressure from a pressure regulating system 33 so that liquid is forced out through outlet 32 under this controlled pressure and will flow at a controlled rate, subject only to variations in the resistance to flow of the load (not shown) to which liquid is being delivered. The pressure applied to vessel 31 from pressure regulating system 33 is held at a predetermined level by a pressure control system 34 which controls gas deliveries from pressure regulating system 33. System 34 keeps the gas pressure at the controlled level as the liquid level in vessel 31 falls with delivery of liquid through outlet 32 and will continue to keep the pressure at this level even if the resistance to flow of the load changes. Also, the rate of liquid delivery can be altered as desired, by altering the gas pressure, under the control of system 34.

Referring back now to FIG. 2, during the re-filling of vessel 11 the flow through outlet 12 is not monitored and it is then not possible to obtain a direct measurement of the flow through outlet 12. This is not important if the resistance to flow from the load is varying only slowly in relation to the time taken to re-fill vessel 11. However, in some applications it is important to be able to obtain a substantially continuous measurement of the flow and the arrangement of FIG. 5 provides for such applications with a further vessel 41 which is connected to be controlled by pressure regulating system 33 and control system 34 to receive the same controlled pressure that is delivered to vessel 31 and to deliver liquid to the same load.

When vessel 31 has to be re-filled, flow is taken from vessel 41 and vice-versa, so that flow and flow measurement are taken alternately from vessel 31 and further vessel 41 and flow to the load is smooth and continuous. A three-way valve 47 enables the flow to outlet 32 to be delivered either from vessel 31 or from further vessel 41.

As with the arrangement of FIG. 2, when liquid is delivered through outlet 12 from vessel 11, the level of liquid in vessel 31 will fall until it reaches a lower acceptable level which is detected by a lower liquid level detector 36. Detector 36 is thus actuated and this causes the system to be re-filled. Now during re-filling, valve 47 effects a change-over and liquid continues to be delivered through outlet 32 from further vessel 41. Control system 34 causes pressure regulating system 33 to continue to apply the same controlled pressure to further vessel 41.

To re-fill vessel 31, a valve 38 is opened allowing liquid to flow from a reservoir 39. Reservoir 39 is pressurised from the high pressure supply 37, avoiding the need for a second pressure regulated output, at a slightly higher pressure than that supplied to vessel 31. Thus, liquid flows from the reservoir 39 into vessel 31 to re-fill it whilst liquid continues to be delivered through outlet 32 from further vessel 41 to the load.

Liquid flowing from reservoir 39 to re-fill vessel 31 has to flow through a restrictor 54 which restricts the flow rate to that for which the pressure regulating system 33 will easily compensate. Such a restrictor could be added to the arrangement of FIG. 2. As liquid continues to re-fill vessel 31 the level of liquid rises until it reaches a higher acceptable level detected by upper liquid level detector 35. This detector is then actuated which causes second valve 38 to be closed completing re-filling.

Throughout the re-filling operation the liquid flow out through outlet 32 continues thus giving, at all times, an uninterrupted, pulsation-free, liquid delivery.

The time taken for the liquid level to fall from the detected upper level to the detected lower level in vessel 41 gives a measure of the rate of liquid delivery to the load whilst vessel 31 is being re-filled and vice-versa. The volume of liquid in vessels 31 and 41 between their respective two detectors is known, so the volume of liquid being delivered can easily be calculated. The pressure delivered by pressure regulating system 33 may then be adjusted more accurately to provide the desired flow rate at outlet 32.

Further vessel 41 can be connected through third valve 48 to reservoir 39 for re-filling and it has level detectors 45 and 46 respectively for detecting the upper and lower acceptable liquid levels. The system 34 controls the opening and closing of valves 38, 47, 48 and 50 and a further three-way valve 53, which is used for controlling pressurisation and venting of reservoir 39, and receives signals from level detectors 35, 36, 45 and 46. A detector 52 is positioned to detect when the tank 51 runs short of liquid so as to prevent gas from entering the liquid system.

In an application such as liquid chromatography, the volumes being handled are quite small, being of the order of micro liters. Whilst the application of the embodiments of the invention shown in the accompanying Figures is not limited specifically to this field, the invention has been found to be particularly useful when used to deliver small volumes. In the arrangements shown in the Figures, the volume between the upper level detectors (5, 15, 15a, 15b, 35, 45) and the lower level detectors (6, 16, 16a, 16b, 36, 46), when used for liquid chromatography, is about 200 micro liters and the delivery rates are between 20 and 400 microliters per minute.

We claim:

1. A system for delivering liquid at a controlled flow rate, the system comprising:
   a vessel having an internal volume for containing a liquid and a pressurized gas and having an outlet for delivery of the liquid, under a gas pressure from the pressurized gas, out of said vessel;
   measuring means, connected to said vessel, for measuring a rate of flow of the liquid out of said vessel, said measuring means comprising upper and lower detectors for detecting the liquid at upper and lower levels, respectively, in said vessel and producing a level signal;
   refilling means, connected to the outlet of said vessel, for delivering an input liquid to said vessel while the liquid continues to be delivered out of said vessel in an uninterrupted, pulsation free stream; and
   controller means, connected to said vessel, said measuring means, and said refilling means, for controlling the gas pressure of the pressurized gas by using the level signal from said measuring means to regulate the rate of flow of the liquid out of said vessel, and for controlling said refilling means by using the level signal from said measuring means to start said refilling means when the liquid is detected at the lower level by said lower detector, and to stop said refilling means when the liquid is detected at the upper level by said upper detector.

2. A liquid delivery system as claimed in claim 1, wherein the measuring means further comprises means for measuring the rate of flow of the pressurized gas into said vessel whereby to derive the rate of flow of the liquid.

3. A liquid delivery system as claimed in claim 1, wherein the measuring means comprises means for measuring the time taken for the liquid in the vessel to fall from said upper level detected by said upper detector to said lower level detected by said lower detector whereby to derive the rate of flow of the liquid.

4. A liquid delivery system as claimed in claim 1, wherein said refilling means comprises a reservoir of the input liquid connected to said vessel for refilling said vessel.

5. A liquid delivery system as claimed in claim 4, wherein said refilling means includes a tank containing the input liquid connected to said reservoir for re-filling said reservoir with the input liquid.

6. A liquid delivery system as claimed in claim 1, wherein said vessel comprises a tube oriented substantially horizontally.

7. A liquid delivery system as claimed in claim 6, wherein said tube is coiled.

8. A liquid delivery system as claimed in claim 1, wherein said vessel has a central area of enlarged cross-section located between an upper and a lower area of smaller cross-section.

9. A liquid delivery system as claimed in claim 8, wherein said measuring means has said upper detector positioned in said upper area of smaller cross-section and said lower detector positioned in said lower area of smaller cross-section.

10. A liquid delivery system according to claim 1, wherein said re-filling means is connected to a source of pressurized gas, whereby the input liquid in said re-filling means is pressurized to a pressure higher than the pressure within said vessel.

11. A liquid delivery system according to claim 10, wherein said source of pressurized gas is also connected to said vessel to deliver said pressurized gas thereto.

12. A system for delivering liquid at a controlled flow rate, the system comprising:
   first and second vessels each having an internal volume for containing a liquid and a pressurized gas and each having an outlet for delivery of the liquid, under a gas pressure from the pressurized gas, out of the vessel;
   a common outlet, connected to each of the outlets said first and said second vessels, for delivery of the liquid under the gas pressure from a respective one of said first and second vessels;
   first and second measuring means, connected to said first and said second vessels, respectively, for measuring a rate of flow of the liquid out of said first and second vessels respectively, said first and second measuring means each comprising an upper detector and a lower detector for detecting the liquid in the respective vessel at an upper level and a lower level, and producing a level signal;
   refilling means, connected to each of the outlets of said first and second vessels, for delivering an input liquid to one of said first and second vessels while the liquid continues to be delivered out of said common outlet in an uninterrupted, pulsation free stream from the other of said first and second vessels;
   switching means connected to the outlets of said first and second vessels and said common outlet; and
   controller means, connected to said first and second vessels, said measuring means, said refilling means, and said switching means, for controlling the gas pressure in said first vessel by using the level signal from said first measuring means to regulate the rate of flow of the liquid out of said first vessel and for controlling the gas pressure in said second vessel by using the level signal from said second measuring means to regulate the rate of flow of the liquid out of said second vessel, said controller means further controlling said refilling means by using the level signals from said first and second measuring means to start said refilling means when the liquid in a respective one of the first and second vessels is detected at the lower level by the respective lower detector, and to stop said refilling means when the liquid in a respective one of the first and second vessels is detected at the upper level by the respective upper detector, and said controller means further controlling said switching means for switching between the outlets of said first and second vessels to allow the liquid to flow from the outlet of one of said vessels to said common outlet while the other of said vessels is being refilled, and to allow the liquid to flow from the outlet of the other of said vessels to said common outlet while said one vessel is being refilled.

13. A liquid delivery system as claimed in claim 12, further comprising a restrictor connected between said re-filling means and said first and said second vessels.

* * * * *